United States Patent [19]

Adams et al.

[11] Patent Number: 5,135,936
[45] Date of Patent: Aug. 4, 1992

[54] ISOMERS OF 1-AZABICYCLO[2.2.2]OCT-3-YL METHYL 1,4-DIHYDRO-2,6-DIMETHYL-4-(3-NITRO-PHENYL)-3,5-PYRIDINEDIACARBOXYLIC AND THEIR USE AS CALCIUM ANTAGONISTS

[75] Inventors: Theodore C. Adams, Perry Hall; Waclaw J. Rzeszotarski, Millersville, both of Md.

[73] Assignee: Marion Merrell Dow Inc., Kansas City, Mo.

[21] Appl. No.: 664,848

[22] Filed: Mar. 5, 1991

[51] Int. Cl.$^5$ .................. C07F 9/06; A61K 31/44
[52] U.S. Cl. ........................ 514/305; 546/137
[58] Field of Search .................. 546/137; 514/305

[56] References Cited

U.S. PATENT DOCUMENTS

| | | | |
|---|---|---|---|
| 2,658,067 | 11/1953 | Duschinsky | 546/137 |
| 3,405,134 | 10/1968 | Judd | 546/137 |
| 3,462,442 | 8/1969 | Biel et al. | 546/137 |
| 4,220,649 | 9/1980 | Kojima et al. | 514/343 |
| 4,501,748 | 2/1985 | Muto et al. | 514/318 |
| 4,593,034 | 6/1986 | Munson, Jr. et al. | 514/305 |
| 4,761,420 | 8/1988 | Genain | 514/336 |
| 4,920,225 | 4/1990 | Genain | 546/21 |

FOREIGN PATENT DOCUMENTS 2122192 6/1983 United Kingdom .

OTHER PUBLICATIONS

Fossheim et al. J. Med. Chem., 1988, 31, 300.
Hof et al., J. Cardiovascular Pharmacol., 1986, 8, 221.
Marciniak et al., J. Med. Chem., 1989, 32, 1402.
Tamazawa et al., J. Med. Chem., 1986, 29, 2504.
Muto et al., Arzneim.-Forsch./Drug Res. 1988, 38, 1662.

*Primary Examiner*—C. Warren Ivy
*Assistant Examiner*—Catherine Scalzo
*Attorney, Agent, or Firm*—Theresa M. Gillis

[57] ABSTRACT

A group of four stereoisomers and their pharmaceutically acceptable salts are disclosed. The stereoisomers have formula I.

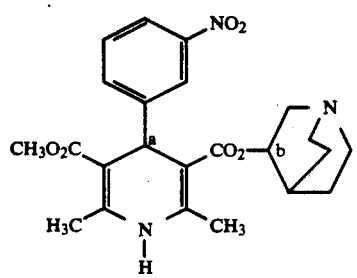

In Formula I the asymmetric centers a and b may be the same or different and have either the absolute R or S configuration. Also disclosed are pharmaceutical compositions containing the stereoisomers and use of the stereoisomers as antihypertensive agents, as peripheral and cerebral vasodilators and as coronary therapeutic agents.

The preferred compound is (R,R)-1-azabicyclo[2.2.2]oct-3-yl methyl 1,4-dihydro-2,6-dimethyl-4-(3-nitrophenyl)-3,5-pyridinedicarboxylate.

5 Claims, No Drawings

ISOMERS OF 1-AZABICYCLO[2.2.2]OCT-3-YL METHYL 1,4-DIHYDRO-2,6-DIMETHYL-4-(3-NITROPHENYL)-3,5-PYRIDINEDICARBOXYLIC AND THEIR USE AS CALCIUM ANTAGONISTS

BACKGROUND OF INVENTION a. Field of Invention

Isomers of 1-azabicyclo[2.2.2]oct-3-yl methyl 1,4-dihydro-2,6-dimethyl-4-(3-nitrophenyl)-3,5-pyridinedicarboxylat and their nontoxic acid addition salts are useful calcium antagonists having utility as antihypertensive agents, as peripheral and cerebral vasodilators and as coronary therapeutic agents.

b. State of the Art

Before the turn of the century some workers postulated that $Ca^{++}$ played a role in the process of muscle contraction. However it was not until 1965, with the discovery of troponin, a $Ca^{++}$ binding protein, that the role of $Ca^{++}$ in the process of muscle contraction was defined. Soon thereafter it was demonstrated that papaverine, an opium alkaloid, and other structurally related compounds known to dilate coronary blood vessels exerted their spasmolytic effect by a $Ca^{++}$ channel antagonist mechanism. This directly led to the development of antagonist drugs. Specifically, it was found that 4-aryldihydropyridines were potent $Ca^{++}$ channel blockers. Nifedipine, dimethyl 1,4-dihydro-2,6-dimethyl4-(2-nitrophenyl)-3,5-pyridinedicarboxylate, is the prototype of such therapeutic agents.

1,4-Dihydropyridines function by slowing the entry of $Ca^{++}$ ions into cells, thereby reducing the force of muscle contraction. Typically, they produce vasodilatation of the peripheral vasculature, especially that of the arteries, to cause a reduction of blood pressure. Clinical applications are particularly directed toward the treatment of oxygen deficiencies of the heart such as angina pectoris and hypertension.

The effects of stereochemistry on the biological actions of this class of pharmacological agent have been studied. For example, the conformation of the dihydropyridine ring, in particular its degree of planarity (R. Fossheim, A. Joslyn, A. J. Solo, E. Luchowski, A. Rutledge, and D.J. Triggle, J. Med Chem., 1988, 31, 300), has been related to potency. Furthermore, when the 3 and 5 ester groups are unsymmetrically substituted, the actions of opposite enantiomers or diastereomers can vary significantly. For example (R. P. Hof, A. Hof, U. T. Ruegg, N. S. Cook, and A. Vogel, J. Cardiovascular Pharmacol., 1986, 8, 221.), the (R)-enantiomer of isopropyl methyl 4-(2,1,3-benzoxadiazol-4-yl) -1,4-dihydro-2,6-dimethyl-3,5-pyridinedicarboxylate (PN 200-110) had almost no effect on heart rate and blood pressure, although it was surprisingly potent in the subendocardium of the left ventricle. On the other hand, the (S)-enantiomer lowered blood pressure and heart rate, whereas both (R)- and (S)-enantiomers increased cardiac output and blood flow to the heart and brain. These results suggest that $Ca^{++}$ channels are able to discriminate between enantiomers and also respond to them differently.

Attempts to increase both potency and clinical selectivity have led to the incorporation of a second center of symmetry into the 1,4-dihydropyridine nucleus wherein one ester moiety is both chiral and basic. For example G. Marciniak, A. Delgado, G. Leclerc, J. Velly, N. Decker and.J. Schwartz, (J. Med. Chem., 1989, 32, 2504.) incorporated a mimic of the known alpha blocker prazosin, into an ester function to give all four enantiomers of the diastereomeric pairs of 2-[N-methyl-N-[(2,3-dihydro-1,4-benzodioxin-2-yl)methyl] amino]ethyl methyl 2,6-dimethyl-4-(3-nitrophenyl)-1,4-dihydropyridine-3,5-dicarboxylate. The (R,R)-enantiomer was the most potent inhibitor of [3H]- nitrendipine binding, whereas the (S,S)-enantiomer was the most potent inhibitor of [3H]-yohimbine binding.

The preparation of the individual enantiomers of the diastereomeric 1-benzyl-3-pyrrolidinyl (K. Tamazawa, H. Arima, T. Kojima, Y. Isomura, M. Okada, S. Fujita, T, Furuya, T. Takenaka, O. Inagaki, and M. Terai, J. Med Chem., 1986, 29, 2504. U.S. Pat. No. 4,220,649) and 1-benzyl-3-piperidinyl (K. Muto, T. Kuroda, H. Kawato, A. Karasawa, K. Kubo, and N. Nakamizo, Arzneim.-Forsch./Drug Res. 1988, 38, 1662, U.S. Pat. No. 4,501,748) esters of methyl 2,6-dimethyl-4-(3-nitrophenyl)-1,4-dihydropyridine-3,5-dicarboxylate have been reported. Both groups reported that the (S,S)-enantiomer exerted the greatest $Ca^{++}$ channel blocking activity as determined by inhibition of [3H]-nitrendipine binding and by lowering of blood pressure in spontaneously hypertensive rats respectively.

The novel isomers of 1-azabicyclo[2.2.2]oct-3-yl methyl 1,4-dihydro-2,6-dimethyl-4-(3-nitrophenyl)-3,5-pyridinedicarboxylate described herein are potent calcium channel antagonists as evidenced by their ability to inhibit $Ca^{++}$ evoked contractions of guinea pig ileum and by their ability to inhibit [3H]-nitrendipine binding. Moreover, it was unexpected that the pharmacological action would be influenced by the bicyclic ester radical to such an extent that the C4 (R) configuration was favored. This was in direct contrast to the generally held belief that the C4 (S) configuration was most active (U.S. Pat. No. 4,761,420) and to analogous diastereomeric dihydropyridines with an asymmetric carbinol carbon in a cyclic amine ester radical, in which the C4 (S) configuration was also most potent (U.S. Pat. Nos. 4,220,649 and 4,501,748).

SUMMARY OF THE INVENTION

The invention provides a group of four stereoisomers of the formula I.

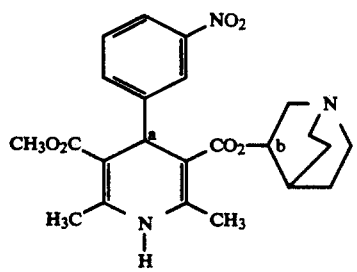

wherein:

The asymmetric centers a and b may be the same or different and have either the absolute R or S configuration. The invention also relates to the pharmaceutically acceptable salts of the foregoing compounds, to pharmaceutical compositions containing effective amounts of such compounds, and to their use as antihypertensive agents, as peripheral and cerebral vasodilators and as coronary therapeutic agents.

DETAILED DESCRIPTION OF THE INVENTION

The compounds of this invention are novel isomers of 1-azabicyclo[2.2.2]oct-3-yl methyl 1,4-dihydro-2,6-dimethyl- 4-(3-nitrophenyl)-3,5-pyridinedicarboxylate of the above formula and their pharmaceutically acceptable salts.

The preferred compound of this invention is (R,R)-1-azabicyclo[2.2.2]oct-3-yl methyl 1,4-dihydro-2,6-dimethyl4-(3-nitrophenyl)-3,5-pyridinedicarboxylate.

The compounds are effective $Ca^{++}$ channel antagonists which gives them therapeutic utility as vasodilators. The invention thus includes pharmaceutical compositions intended for such uses which comprise an effective amount of the individual isomers and a pharmaceutically acceptable carrier. The invention also includes methods of using the novel compounds as $Ca^{++}$ channel antagonists and to treat a variety of cardiovascular disorders by treating hypertension or producing hypotension.

It has been found that the pharmacological action of the 1,4-dihydropyridines is dependent upon configuration, and that one of the enantiomers of a diastereomeric pair is always significantly more potent than its antipode. Surprisingly, the pharmacological action of the compounds is primarily influenced by the bicyclic ester radical with the C4 (R) configuration being favored.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicyclic, methanesulfonic, ethanedisulfonic, acetic, malic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

The compounds of this invention may be administered orally or parenterally in conventional dosage unit forms such as tablets, capsules, injectables, aerosols, or the like, by incorporating the appropriate dose of a compound of the indicated formula with carriers according to accepted pharmaceutical practices.

Preferably a compound or an acid addition salt thereof is administered orally to an animal (including a human) in a tablet or capsule comprising an amount sufficient to produce the desired activity. Each dosage unit will contain the active ingredient in an amount of about 10 mg to about 400 mg, preferably from about 30 mg to about 200 mg. Advantageously equal doses will be administered 2 to 4 times daily. The daily dosage regimen will generally be about 60 mg to about 600 mg, preferably from about 100 mg to about 300 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be about 25 mg to about 1 g. If a liquid carrier is used, the preparation will be in the form of a syrup, emulsion, soft gelatin capsule, sterile injectable liquid such as an ampoule, or an aqueous or nonaqueous liquid suspension.

The compounds of the invention can be prepared by esterification of the enantiomers of methyl 3-carboxy-1,4-dihydro-2,6-dimethyl-4-(3-nitrophenyl)-5-pyridinedicarboxylate with the enantiomers of 1-azabicyclo[2.2.2]octan-3-ol (3-quinuclidinol). The acid may be prepared by condensation of 3-nitrobenzaldehyde with methyl 3-aminocrotonate and 2-cyanoethyl acetoacetate to afford 2-cyanoethyl methyl 1,4-dihydro-2,6-dimethyl-4-(3-nitrophenyl)-3,5-pyridinedicarboxylate which may be hydrolyzed with one equivalent of a suitable base (G.B. Patent 2122192), e.g. NaOH, to give methyl 3-carboxy-1,4-dihydro-2,6-dimethyl-4-(3-nitrophenyl)-5-pyridinedicarboxylate. Resolution of the acid is achieved by recrystallization of the cinchonidine (U.S. Pat. No. 4,920,225) addition salt from ethanol free chloroform. The enantiomers of 3-quinuclidinol are obtained by the procedure of B. Ringdahl, B. Resul and R. Dahlbom (Acta. Pharm. Seuc., 1979, 16, 281).

The following examples are illustrative of the invention. Temperature is expressed in degrees Celsius; NMR signals are given as ppm downfield from an internal standard of tetramethylsilane.

EXAMPLE I

Methyl 3-carboxy-1,4-dihydro-2,6-dimethyl-4-(3-nitrophenyl)-5-pyridinedicarboxylate Methyl 3-aminocrotonate, 9.45 g (62.6 mmol), was stirred in 30 mL of methanol with 7.2 g (62.6 mmol) 2-cyanoethyl acetoacetate and 9.7 g (62.6 mmol) of 3-nitrobenzaldehyde for 2 h at room temperature before refluxing 3.5 h. The resulting mixture was cooled and placed in the freezer overnight. The resulting solid was recrystallized twice from methanol to give 5.9 g of pure product. The mother liquors were chromatographed on silica gel with 3 7, EtAc: petroleum ether to give 9.4 g of 2-cyanoethyl methyl 3-carboxy-1,4-dihydro-2,6-dimethyl-4-(3-nitrophenyl)-5-pyridinedicarboxylate.

2-Cyanoethyl methyl 1,4-dihydro-2,6-dimethyl-4-(3-nitrophenyl)-3,5-pyridinedicarboxylate, 5.9 g (15.2 mmol), was stirred to solution in 70 mL of THF and cooled with ice before 33 mL of 0.5 N NaOH (16.5 mmol) was added dropwise. The mixture was stirred 4 h at room temperature before pouring onto 100 mL of water and extracting with ethyl acetate (4×100 mL). The cooled mixture was acidified with 1.3 mL of con HCl before placing in a refrigerator overnight. The solid was filtered and recrystallized from acetonitrile to give methyl 3-carboxy-1,4-dihydro-2,6-dimethyl-4-(3-nitrophenyl)-5-pyridinedicarboxylate. 1H NMR (DMSO-d6) δ2.31(s, 6H), 3.60(s, 3H), 5.03(s, 1H), 7.52–7.67(m, 2H), 7.92–8.06(m, 1H), 8.92–9.01(m, 1H).

EXAMPLE II (S)-Methyl 3-carboxy-1,4-dihydro-2,6-dimethyl-4-(3-nitrophenyl)-5-pyridinedicarboxylate Cinchonidine, 53.56 g (.165 M) and 54.88 g (.165 M) of methyl 3-carboxy-1,4-dihydro-2,6-dimethyl-4-(3-nitrophenyl)-5-pyridinedicarboxylate, were dissolved in hot 95% ethanol and the solvents removed at reduced pressure. The resulting solid was dissolved in a minimum of hot ethanol free chloroform and allowed to stand two days at room temperature. The resulting crystals (47.4 g) were recrystallized three times from ethanol free chloroform to give the (+)-acid salt. This cinchonidine salt was dissolved in acetone and 1N HCl added. The acetone was removed at reduced pressure and the resulting solid collected and recrystallized from methanol to give 6.6 g, $[\alpha]^{24}{}_d = +19.7°$ (c=.60, acetone) of (S)-methyl 3-carboxy-1,4-dihydro-2,6-dimethyl-4-(3-nitrophenyl)-5-pyridinedicarboxylate.

EXAMPLE III (R)-Methyl 3-carboxy-1,4-dihydro-2,6-dimethyl-4-(3-nitrophenyl)-5-pyridinedicarboxylate The mother liquors from the initial chloroform crystallization were concentrated and crystallized twice from ethanol free chloroform and the resulting mother liquors evaporated at reduced pressure to give the cinchonidine (−)-acid salt. This salt was dissolved in acetone and mixed with 1N HCl, the acetone was removed at reduced pressure and the resulting solid recrystallized from methanol to give 8.1 g, $[\alpha]^{24}{}_d = -19.8°$ (c=.55, acetone) of (R)-methyl 3-carboxy-1,4-dihydro-2,6-dimethyl-4-(3-nitrophenyl)-5-pyridinedicarboxylate.

EXAMPLE IV (S,S)-1-Azabicyclo[2.2.2]oct-3-yl methyl 1,4-dihydro-2,6-dimethyl-4-(3-nitrophenyl)-3,5-pyridinedicarboxylate (S)-Methyl 3-carboxy-1,4-dihydro-2,6-dimethyl-4-(3-nitrophenyl)-5-pyridinedicarboxylate, 2.0 g (6.0 mmol), was suspended in 10 mL of methylene chloride at −10° C. under nitrogen. Trifluoroacetic anhydride (4.5 mL) was added and after 1.5 h solution was attained and the solvents were evaporated at reduced pressure without warming. The residue was dissolved in 10 mL methylene chloride and cooled to −10° C. before 0.84 g (6.6 mmol) (S)-3-quinuclidinol was added. After stirring 1.5 h the mixture was poured onto (sat) NaHCO$_3$, the organics were dried (MgSO$_4$), and the solvents were evaporated at reduced pressure to a foam that solidified. The residue was chromatographed (silicAR, EtAc, then 25% methanol in EtAc) before final purification on preparative tlc (alumina, 1.5 mm×20 cm×20 cm, 9: 1, EtAc: MeOH). The product was converted to its hydrochloride to give (S,S)-1-azabicyclo[2.2.2]oct-3-yl methyl 1,4-dihydro-2,6-dimethyl-4-(3-nitrophenyl)-3,5-pyridinedicarboxylate, hydrochloride $[\alpha]^{25}{}_d = -55.3°$ (c=0.0034, MeOH). IR(KBr) 1697, 1527 cm −1; 1H NMR (CDCl$_3$) δ1.4–2.1(m, 4H), 2.3(s, 3H), 2.35(s, 3H), 2.3–3.2(m, 6H), 3.63(s, 3H), 4.6–4.9(m, 1H), 5.12(s, 1H), 6.55(s, 1H), 7.2–8.2(m, 4H). Anal. calcd. for C$_{23}$H$_{27}$N$_3$O$_6$. HCl . 0.5 H$_2$O: C, 56.71; H, 6.00; N, 8.50. Found: C, 56.30; H, 6.23; N, 8.66.

EXAMPLE V (S,R)-1-Azabicyclo[2.2.2]oct-3-yl methyl 1,4-dihydro-2,6-dimethyl-4-(3-nitrophenyl)-3,5-pyridinedicarboxylic acid (S)-Methyl 3-carboxy-1,4-dihydro-2,6-dimethyl-4-(3-nitrophenyl)-5-pyridinedicarboxylate, 1.3 g (4.0 mmol), was suspended in 8 mL of methylene chloride at −10° C. under nitrogen. 2.5 mL Trifluoroacetic anhydride was added and after 1.5 h solution was attained and the solvents were evaporated at reduced pressure without warming. The residue was dissolved in 8 mL methylene chloride and cooled to −10° C. before 0.57 g (4.4 mmol) (R)-3-quinuclidinol was added. After stirring 0.75 h the mixture was poured onto (sat) NaHCO$_3$, the organics were dried (MgSO$_4$), and the solvents were evaporated at reduced pressure to a foam that solidified. The residue was chromatographed (silicAR, EtAc, then 10% methanol in EtAc) to give a product that was chromatographed (neutral alumina activity IV, EtAc, then chloroform) to give the pure product which was converted to its hydrochloride to give (S,R)-1-azabicyclo[2.2.2]oct-3-yl methyl 1,4-dihydro-2,6-dimethyl- 4-(3-nitrophenyl)-3,5pyridinedicarboxylate, hydrochloride $[\alpha]^{25}{}_d = -90.4°$ (c=.0026, MeOH). IR(KBr) 1697, 1527, 1491, 1344 cm −1; 1H NMR (CDCl$_3$) δ1.7–2.1(m, 4H), 2.2–2.4(m, 1H), 2.38(s, 3H), 2.42(s, 3H), 3.0–3.4(m, 5H), 3.4–3.7(m, 1H), 3.67(s, 3H), 4.8–5.1(m, 1H), 5.04(s, 1H), 6.73(s, 1H), 7.3.81(m, 4H). Anal. calcd. for C$_{23}$H$_{27}$N$_3$O$_6$. HCl . H$_2$O: C, 55.68; H, 6.09; N, 8.50. Found: C, 55.82; H, 5.90; N, 8.29.

EXAMPLE VI (R,R)-1-Azabicyclo[2.2.2]oct-3-yl methyl 1,4-dihydro-2,6-dimethyl-4-(3-nitrophenyl)-3,5-pyridinedicarboxylate (R)-methyl 3-carboxy-1,4-dihydro-2,6-dimethyl-4-(3-nitrophenyl)-5-pyridinedicarboxylate, 1.74 g (5.2 mmol) (−11.6°, 60% ee), was suspended in 10 mL of methylene chloride at −10° C. under nitrogen. 4.5 mL of trifluoroacetic anhydride was added and after 1.5 h solution was attained and the solvents were evaporated at reduced pressure without warming. The residue was dissolved in 10 mL methylene chloride and cooled to −10° C. before 0.75 g (5.9 mmol) (R)-3-quinuclidinol was added. After stirring 1 h the mixture was poured onto 35 mL (sat) NaHCO$_3$, the organics were dried (MgSO$_4$), and the solvents were evaporated at reduced pressure to a foam that solidified. The residue was chromatographed (silicAR, 6 in×40 mm, EtAc then 2, 5, 10, and 25% MeOH in EtAc), the desired fractions being combined before chromatography (neutral alumina, activity IV, 100 g, chloroform, then 0.12, 0.25, 0.75, and 1.5 ethanol in chloroform). The desired fractions were combined and mixed with 2 mL 2 N HCl in ethanol. The solvents were evaporated at reduced pressure, and the resulting hydrochloride salt dried to give (R,R)-1-azabicyclo[2.2.2]oct3-yl methyl 1,4-dihydro-2,6-dimethyl-4-(3-nitrophenyl)3,5-pyridinedicarboxylate, hydrochloride $[\alpha]^{25}{}_d = 55.3°$ (c=0.0017, MeOH). IR(KBr) 1694, 1529, 1488, 1349, 1216 cm −1; 1H NMR (CDCl$_3$) δ1.7–2 3(m, 5H), 2.38(s, 3H), 2.44(s, 3H), 2 6–3.6(m, 7H), 3.67(s, 3H), 4.8–5.1(m, 2H), 7.3–8.2(m, 5H). Anal calcd. for C$_{23}$H$_{27}$N$_3$O$_6$.HCl 2H$_2$O: C, 53 73; H, 6.27; N, 8.20. Found: C, 53.53; H, 5.85; N, 8.13.

EXAMPLE VII (R,S)-1-Azabicyclo[2.2.2]oct-3-yl methyl 1,4-dihydro-2,6-dimethyl-4-(3-nitrophenyl)3,5-pyridinedicarboxylate (R)-Methyl 3-carboxy-1,4-dihydro-2,6-dimethyl-4-(3-nitrophenyl)-5-pyridinedicarboxylate, 2.0 g (6.0 mmol) (−11.6°, 60% ee), was suspended in 10 mL of methylene chloride at −10° C. under nitrogen. 5.0 mL Trifluoroacetic anhydride was added and after 1.5 h solution was attained and the solvents were evaporated at reduced pressure without warming. The residue was dissolved in 10 mL methylene chloride and cooled To −10° C. before 0.85 g (6.6 mmol) (S)-3-quinuclidinol was added. After stirring 1 h the mixture was poured onto 35 mL (sat) NaHCO$_3$, the organics were dried (MgSO$_4$), and the solvents were evaporated at reduced pressure to a foam that solidified. The residue was chromatographed (silicAR, EtAc then 2, 5, 10, and 25% methanol in EtAc) the desired fractions being combined before chromatography (neutral alumina, activity IV, 100 g, chloroform, then 0.12, 0.25, 0.75, and 1.5% ethanol in chloroform). The desired fractions were combined and mixed with 2 mL of 2 N HCl in ethanol. The solvents were evaporated at reduced pressure, and the resulting hydrochloride salt dried to give (R,S)-1-azabicyclo[2.2.2]oct-3-yl methyl 1,4-dihydro-2,6-dimethyl-4-(3-nitrophenyl)-3,5-pyridinedicarboxylate, hydrochloride $[\alpha]^{25}_d = 86.8°$ (c=0.0022, MeOH). IR(KBr) 1697, 1535, 1488, 1349, 1216 cm$^{-1}$; $^1$H NMR (CDCl$_3$) δ1.3-2.2(m, 5H), 2.32(s, 3H), 2.4(s, 3H), 2.4-3.3(m, 6H), 3.67(s, 3H), 4.66(m, 1H), 5.13(s, 1H), 6.86(s, 1H), 7.2-8.3(m, 4H). Anal. calcd. for C$_{23}$H$_{27}$N$_3$O$_6$ . HCl . H$_2$O: C, 55.68; H, 6.09; N, 8.50. Found: C, 55.69; H, 5.97; N, 8.37.

EXAMPLE VIII

Calcium Channel Antagonist Activity in Guinea Pig Isolated Ileal Smooth Muscle

Male albino guinea pigs are sacrificed by stunning and exsanguination. The abdominal cavity is opened and the small intestine is removed, with about 10 cm of the terminal ileum being discarded. The tissue is placed in a dish containing Tyrode's solution of the following composition (in mM): NaCl 136.90; KCl 2.68; NaHCO$_3$ 11.90; NaH$_2$PO$_4$ 0.36; MgCl$_2$ 0.98; CaCl$_2$ 1.77; dextrose 5.55 and cut into three to four segments. A glass rod (6 mm diameter) is carefully inserted into the lumen of each segment and excess connective tissue or fat is removed. The longitudinal smooth muscle is carefully separated from the underlying circular muscle layer by gently stroking a moist cotton swab on a tangent to shallow, longitudinal incisions made parallel to the mesenteric attachment. Using gentle traction, and taking care to keep the segment moist at all times, the preparation is stripped from the remaining length of the ileal segment (Paton, W. D. M.; Zar, M. A.; J. Physiol. 1968, 194, 13.)

Each preparation is suspended in a 10 mL jacketed glass tissue bath containing Tyrode's solution maintained at 37° C. and gassed with 5% CO$_2$ in O$_2$. The preparation is attached by silk thread to a force-displacement transducer. Tension changes are recorded isometrically and displayed on a chart recorder. The initial resting tension is adjusted to 0.5 g and the preparation equilibrated for 55 min prior to experimentation. At the end of this period, the bathing solution is replaced with Ca$^{++}$ free Tyrode's solution. This solution is prepared by omitting CaCl2. The preparation is washed four times in Ca$^{++}$ free Tyrode's solution to remove any Ca$^{++}$ remaining in the bath, and allowed to equilibrate for a further 20 min.

Experimental Protocol. Concentration-response curves to CaCl$_2$ are obtained using the following procedure. Preparations are exposed to a depolarizing concentration of KCl (80 mM) for 6 min. At the end of this period CaCl$_2$ is added to the bath cumulatively in the concentration range 0.2–8.0 mM. Successive additions of each Ca$^{++}$ concentration are carried out only when the previous response has reached a plateau. When the maximum response has been attained the bath is again washed (five times) with Ca$^{++}$ free buffer, and the preparation re-equilibrated for approximately 15 min. A second Ca$^{++}$ concentration-response curve is then obtained in the same manner. This second curve serves as control for that tissue.

Further curves are obtained in the presence of increasing concentrations of the test drugs. Where appropriate, the test drug is added to the bath immediately following addition of KCl, and 6 minutes later the concentration-response curve to Ca$^{++}$ is obtained. Each test preparation is exposed to three different concentrations of a test drug.

For each ileal preparation, the control EC$_{50}$ for Ca$^{++}$ the concentration producing 50% of the maximum response) is determined from the control concentration- response curve. Calcium blocking activity is defined as a Kb value (the concentration producing a two-fold rightward shift in the control curve), calculated from EC$_{50}$ ratios in the absence and presence of test drugs.

TABLE I

| Inhibition of Ca$^{++}$ evoked contractions in Guinea Pig Ileum | |
|---|---|
| Compound | Kb (nM) |
| (R,R)-I | 34.0 |
| (R,S)-I | 174.0 |
| (S,S)-I | 1621.8 |
| (S,R)-I | 3164.5 |

EXAMPLE IX

[3H]-Nitrendioine Bindino in Rat Cortex

Animals were decapitated and the cortical tissue was dissected, weighed and polytroned in about 20 volumes (w/v) of ice cold buffer (50 nM TRIS HCl, pH 7.5). The tissue was then washed 3 times via centrifugation (20,000 rpm for 10 min at 4° C.) with subsequent resuspension in fresh buffer. The final pellet was resuspended prior to the assay at 22.5 mg/mL of [3H]-nitrendipine. Incubations were performed at room temperature for 90 min in each assay. These incubations were done in triplicate in a final assay volume of 2.0 mL. Non-specific binding was determined by the addition of 1 uM nifedipine for the [3H]-nitrendipine assay each to triplicate set of tubes. Reactions in each assay were terminated by filtration using a Brandel Cell Harvester followed by washing with ice cold buffer.

For preliminary evaluations in each assay, all compounds were examined at four log concentrations (1 nM−1 uM). full displacement curves were generated on all compounds showing inhibition of specific binding of 50% or greater at a 1 uM drug concentration. Standard reference compounds were included and evaluated in each assay. Analysis of data was done using both the EBDA Scafit program and HP-11C linear regression.

TABLE II

| Inhibition of [3H]-Nitrendipine Binding in Rat Cortical Membranes | | |
|---|---|---|
| Compound | Ki (nM) | Slope |
| (R,R)-I | 11.0 | 1.02 |
| (R,S)-I | 56.0 | 0.99 |
| (S,S)-I | >10 uM | — |
| (S,R)-I | >10 uM | — |

What is claimed is:
1. A compound of the formula:

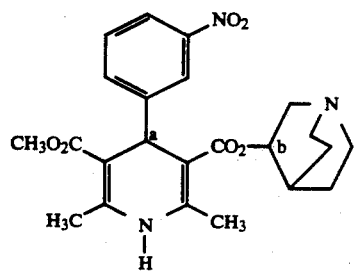

wherein a and b designate the asymmetric centers and the pharmaceutically acceptable salts thereof.

2. The compound of claim 1 wherein the center (b) is (R) and the center (a) is (R).

3. The compound of claim 1 wherein the center (b) is (S) and the center (a) is (R).

4. A pharmaceutical composition comprising the compound of claim 1 and a pharmaceutically acceptable carrier.

5. A method for treating hypertension comprising administering to a host the composition of claim 4.

* * * * *

UNITED STATES PATENT AND TRADEMARK OFFICE
CERTIFICATE OF CORRECTION

PATENT NO. : 5,135,936

DATED : August 4, 1992

INVENTOR(S) : Theodore Claude Adams and Waclaw J. Rzeszotarski

It is certified that error appears in the above-indentified patent and that said Letters Patent is hereby corrected as shown below:

On the title page, item [54] "PYRIDINEDIACARBOXYLIC" should read —PYRIDINEDICARBOXYLATE—

At Column 1, line 5, the patent reads "pyridinediacarboxylic" and should read --pyridinedicarboxylate--.

At Column 1, line 12, the patent reads "pyridinedicarboxylat." and should read --pyridinedicarboxylate--.

At Column 1, lines 29 and 30, the patent reads "dimethyl4" and should read --dimethyl-4--.

At Column 3, line 10, the patent reads "dimethyl4" and should read -dimethyl-4--.

At Column 4, line 44, the patent reads "37" and should read --3: 7--.

At Column 5, line 10, the patent reads "$[\alpha]24d =$" and should read --$[\alpha]24 =$--.

At Column 5, line 24, the patent reads "$[\alpha]24d =$" and should read --$[\alpha]24 =$--.

At Column 5, line 50, the patent reads "$[\alpha]25d =$" and should read --$[\alpha]24 =$--.

At Column 6, line 13, the patent reads "$[\alpha]25d =$" and should read --$[\alpha]25 =$--.

At Column 6, line 35, the patent reads "0.75" and should read --.75 g--.

At Column 6, line 47, the patent reads "'OCT3-yl" should read —OCT-3-yl—

At Column 6, line 49, the patent reads "$[\alpha]25d = 55.3° (c = 0.0017,$" and should read --$[\alpha]25 = 55.3° (c = .0017,$--.

At Column 7, line 15, the patent reads "$[\alpha]25d =$" and should read --$[\alpha]25 =$--.

At Column 8, line 33, the patent reads "Nitrendioine" and should read --Nitrendipine--.

UNITED STATES PATENT AND TRADEMARK OFFICE
CERTIFICATE OF CORRECTION

PATENT NO. : 5,135,936

DATED : August 4, 1992

INVENTOR(S) : Theodore Claude Adams and Waclaw J. Rzeszotarski

It is certified that error appears in the above-indentified patent and that said Letters Patent is hereby corrected as shown below:

At Column 10, line 7, the patent reads "comprising the compound" and should read —comprising an effective amount of the compound—.

Signed and Sealed this

Sixteenth Day of August, 1994

Attest:

BRUCE LEHMAN

Attesting Officer — Commissioner of Patents and Trademarks